US00RE49974E

(19) United States
(12) Reissued Patent
Craig

(10) Patent Number: US RE49,974 E
(45) Date of Reissued Patent: May 21, 2024

(54) DENTAL CARIES STATUS DISCLOSING SOLUTIONS

(71) Applicant: R.M CREIGHTON DENTAL PTY LTD, Clontarf (AU)

(72) Inventor: Graham Craig, Balgowlah (AU)

(73) Assignee: R.M CREIGHTON DENTAL PTY LTD (AU)

(21) Appl. No.: 17/387,534

(22) Filed: Jul. 28, 2021

Related U.S. Patent Documents

Reissue of:
(64) Patent No.: 10,610,468
Issued: Apr. 7, 2020
Appl. No.: 16/336,451
PCT Filed: Sep. 29, 2017
PCT No.: PCT/AU2017/051071
§ 371 (c)(1),
(2) Date: Mar. 25, 2019
PCT Pub. No.: WO2018/058199
PCT Pub. Date: Apr. 5, 2018

(30) Foreign Application Priority Data

Sep. 30, 2016 (AU) ..... 2016903971

(51) Int. Cl.
*A61K 8/19* (2006.01)
*A61K 8/20* (2006.01)
*A61K 8/21* (2006.01)
*A61Q 11/00* (2006.01)

(52) U.S. Cl.
CPC ..... *A61K 8/19* (2013.01); *A61K 8/20* (2013.01); *A61K 8/21* (2013.01); *A61Q 11/00* (2013.01); *A61K 2800/42* (2013.01); *A61K 2800/884* (2013.01)

(58) Field of Classification Search
CPC ... A61K 8/19; A61K 8/20; A61K 8/21; A61K 2800/42; A61K 2800/884; A61Q 11/00
See application file for complete search history.

(56) References Cited

U.S. PATENT DOCUMENTS 3,567,823 A 3/1971 Yamaga et al. ..... A61K 8/21 424/673
3,995,371 A * 12/1976 O'Keefe ..... A61C 5/00 427/304
6,461,161 B1 10/2002 Ngo et al.
2005/0239004 A1* 10/2005 Gahler ..... C03C 17/10 430/212

FOREIGN PATENT DOCUMENTS

AU 554112 B2 8/1986

OTHER PUBLICATIONS

Craig et al., "Caries progression in primary molars: 24-month results from a minimal treatment programme", 1981, Munksgaard, Copenhagen, Community Dent.. Oral Epidemiol, pp. 260-265.
Craig G.G. et al.: "Clinical evaluation of a modified silver fluoride application technique designed to facilitate lesion assessment in outreach programs", BMC Oral Health, 2013, vol. 13, Article 73.
Horst et al., "UCSF Protocol for Caries Arrest Using Silver Diamine Fluoride: Rationale, Indications, and Consent", J Calif Dent Assoc. Jan. 2016 ; 44(1): 16-28.
Howell, et al., "Effect of topically applied stannous fluoride on dental caries experience in children", J Am Dent Assoc. Jan. 1955;50(1):14-7.
https://mms.mckesson.com/product/1030153/StatLab-Medical-Products-SSC-SNX065 (previously http://www.statlab.com/he-consumables/stains/special-stain-components/silver-nitrate-solution-0-2.html).
hittps://www2.le.ac.ukklepartments/csmm/internal-information/procedures/reagent-production/107.pdf.
International Search Report dated Nov. 30, 2017 from PCT Application No. PCT/AU2017/051071.
Nishino et al., "Effect of Topically applied ammoniacal silver fluoride on dental caries in children", J. Osaka Univ.. Dent. Sch., vol. 9, 149-155, 1969.

* cited by examiner

*Primary Examiner* — Norca L. Torres Velazquez
(74) *Attorney, Agent, or Firm* — Mendelsohn Dunleavy, P.C.

(57) ABSTRACT

There is provided herein a dental Caries Status Disclosing Solution comprising a water-based silver fluoride solution for use in the initial application of the silver fluoride solution to a carious lesion followed by the subsequent application of a reducing agent solution for the visual analysis of the status of the carious lesion wherein the water-based silver fluoride solution comprises nitric acid to stabilise the water-based silver fluoride solution.

19 Claims, No Drawings

DENTAL CARIES STATUS DISCLOSING SOLUTIONS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

FIELD OF THE INVENTION

The present invention relates to dental staining solutions and in particular, but not necessarily entirely, to dental Caries Status Disclosing Solutions (CSDS).

BACKGROUND OF THE INVENTION

Carious lesion staining solutions, referred to herein as dental Caries Status Disclosing Solutions (CSDS) are presently used in dentistry to indicate caries status.

CSDS stems from early clinical use of water-based silver fluoride followed by stannous fluoride, wherein it was an empirical observation that treated carious lesions that remained black had not progressed (Craig et al., 1981). To investigate this aspect further a clinical trial was conducted to determine whether this phenomenon was, in effect, a reliable indicator of lesion progression. The results indicated that it was (Craig et al., 2013). As such, the combination of silver fluoride followed by stannous fluoride became the basis for CSDS.

CSDS is applied to active carious lesions in primary molars in children, root surface caries, prophylactically, on recurrent caries around restorations and crown and bridgework in the elderly.

The water-based silver fluoride is applied first and, one to three minutes later, the stannous fluoride is placed and acts as a reducing agent for the silver.

The procedure stains an active carious lesion black. If the lesion remains black over a period of time it is an indication that the caries is not progressing (i.e. caries is arrested).

However, if the lesion starts to lighten it is an indication that the caries is progressing.

As such, CSDS is a visual indicator of the status of a carious lesion; namely if it has been arrested or still progressing.

The CSDS may comprise 40% (w/v) silver fluoride and 10% (w/v) stannous fluoride.

Both silver fluoride and stannous fluoride have separately been used as topical agents for various purposes in dentistry for several decades.

For example, an ammoniated version of silver fluoride (38% silver diammine fluoride) was first used in Japan to treat carious lesions in primary teeth (Nishino et al., 1969). Stannous fluoride, at a concentration of 8-10%, was first used in the US as a topical fluoride agent to prevent dental caries. (Howell et al., 1955).

Furthermore, a water-based version of silver fluoride was first used in Australia in the later 1970s in a clinical treatment program for anxious children in Bourke NSW (Craig et al., 1981). The silver fluoride and stannous fluoride used in the study were manufactured and marketed by Creighton Pharmaceuticals of Double Bay NSW and were sold from 1978 to 2002.

Now, a problem exists with the use of silver fluoride in that the silver ion levels in silver fluoride is reduced over time by the adsorption of silver to the container walls. Silver ions have the tendency to "clump" once reduced to metallic silver and so the depletion of silver ions from solution can be marked.

For example, a laboratory evaluation conducted by Dr GG Craig found a water-based 40% (w/v) silver fluoride solution showed a 30% reduction in silver ion levels after aging at 55° C. for 30 days. This testing process is known as aged testing where the temperature is raised above ambient such that 55° C. for 30 days is in fact equivalent to 9 months at ambient temperature of 23° C.

In terms of silver diammine fluoride, ammonia has been used as a stabilising agent to prevent the precipitation of metallic silver from solution. The use of ammonia forms the silver complex $Ag(NH_3)_2^+$.

Presently, all manufacturers producing silver fluoride dental solution known to the Inventor utilise ammonia for the stabilisation of the solution:

| Product | Manufacturer | Stabiliser |
|---|---|---|
| Saforide | Toyo Seiyaku Kasei, Japan | Ammonia |
| Riva Star | SDI, Bayswater, Victoria | Ammonia |
| Advantage Arrest | Elevate Oral Care, West Palm Beach, Florida | Ammonia |
| Cariestop (Not straight silver fluoride uses a complicated formula to produce silver and fluoride ions). | Biodinamica, Brazil | Uses silver nitrate, boron fluoride in hydrofluoric acid, ammonia hydroxide and water. |

However, the use of ammonia as a stabilising agent has disadvantages in terms of smell and the potential for a transitory gingival burn. Although the burn is normally gone after 24 hours it is recommended that the gingival contact by the solution be minimised or avoided completely.

Specifically, according to Horst et al., 2016, in 9 randomized clinical trials involving children or elders monitored for 1-3 years in which silver diammine fluoride was applied to multiple teeth to arrest or prevent dental caries, a mildly painful white lesion side effect in the mucosa was noted in a portion of the subjects, which disappeared at 48 hours without treatment. The occurrence of reversible localized changes to the oral mucosa was recognised in the first reports of longitudinal studies.

As such all current manufacturers of silver diammine fluoride for dental use recommend protection of the gingiva (gums) during the topical application of the solution.

Furthermore, the Australian Centre for Population Oral Health (ARCPOH) in Adelaide sought, by way of personal communication with the present Inventor, a water-based version of silver fluoride on account of the ammoniated version of silver fluoride not being received well by the elderly involved in a study into the effect of silver diammine fluoride in preventing root surface caries.

As such, a need therefore exists for a method of stabilising silver fluoride which will overcome or substantially ameliorate at least some of the deficiencies of the prior art, or to at least provide an alternative.

It is to be understood that, if any prior art information is referred to herein; such reference does not constitute an admission that the information forms part of the common general knowledge in the art, in Australia or any other country.

SUMMARY OF THE DISCLOSURE

We discovered that, in one experiment, the addition of 3-5% (w/v) nitric acid, using ultra-pure water purged with argon gas, to a CSDS silver fluoride solution brought the pH down to pH 5.5-6.0 and resulted in there being substantially no observed change in silver ion levels after aging at 55° C. for 60 days, (thereby being equivalent to 18 months at an ambient temperature of 23° C.).

As such, we found that the addition of the small amount of nitric acid to the water-based silver fluoride solution unexpectedly markedly increased the longevity of the silver ions and that therefore that nitric acid can be used a suitable stabiliser for CSDS silver fluoride solutions in the dental industry.

To date, ammonia has typically been used as a stabiliser for a very long period including, as alluded to above, since at least 1969 in Japan albeit with the disadvantages of the unpleasant smell and the burning of the mucosa.

Furthermore, all silver fluoride manufacturers presently known to the Inventor, including those listed above, utilise ammonia for the stabilisation of silver fluoride.

As such, the present utilisation of nitric acid can be said to be satisfying a long felt need.

Moreover, manufacturers[1] of silver nitrate solutions used in vitro for staining histological sections currently recommend refrigeration for preserving the shelf life up to 18 months.

[1]http://www.statlab.com/he-consumables/stains/special-stain-component/silver-nitrate-solution-0-2.html (accessed 19/08/2016)

It should be noted that silver nitrate and silver fluoride are by far the most soluble silver salts and, with silver fluoride, no reports have been found of silver fluoride being used in vitro to stain histological sections.

Furthermore, other manufacturers[2] of silver nitrate solutions, used in vitro for staining histological sections, only recommend a shelf life of up to 6 months without refrigeration.

[2]https://www2.le.ac.uk/departments/csmm/internal-information/procedures/reagent-production/107.pdf Conversely, the utilisation of nitric acid as a stabiliser as is described herein allows for water-based silver fluoride solutions to have a shelf month of approximately 24 months or more without refrigeration.

As such, with the foregoing in mind, in accordance with one aspect, there is provided dental Caries Status Disclosing Solutions comprising a water-based silver fluoride solution for use in the initial application of the silver fluoride solution to a carious lesion followed by the subsequent application of a reducing agent solution for the visual analysis of the status of the carious lesion wherein the silver fluoride solution comprises nitric acid to stabilise the silver fluoride solution.

The silver fluoride solution may comprise silver fluoride 2% to 75% (w/v).

The nitric acid substantially may stabilise the silver fluoride solution such that the silver ion levels do not decrease by more than 5% over a period of at least 9 months at approximately 25° C.

The nitric acid substantially may stabilise the silver fluoride solution such that the silver ion levels do not decrease by more than 5% over a period of up to 24 months at approximately 25° C.

The nitric acid may be approximately 3-5% (w/v of the final solution.

The nitric acid may be added to bring the pH of the silver fluoride solution down to approximately pH 5.5-6.0.

The water may be ultrapure water.

The water may be purged with argon gas.

The reducing agent solution may comprise an inorganic metallic salt.

The metallic salt may have a concentration between 1% to 50% (w/v) of the reducing agent solution.

The metallic salt may be ferrous fluoride.

The metallic salt may be stannous fluoride.

Glycerol may be added during the preparation of the stannous fluoride to reduce hydrolysis of the reducing agent solution.

The reducing agent solution may be hand mixed.

The reducing agent solution comprising an organic reducing agent.

The organic reducing agent may have a concentration of between 1% to 50% (w/v) the reducing agent solution.

The organic reducing agent may comprise tannic acid.

The organic reducing agent may comprise a polyphenol.

The organic reducing agent may comprise eugenol.

The organic reducing agent may comprise a phenylpropanoid.

The reducing agent solution comprising a sugar.

The sugar may comprise an oligosaccharide.

The sugar may comprise a polysaccharide.

The sugar may comprise a monosaccharide.

The sugar may comprise a disaccharide.

The monosaccharide may comprise at least one of aldoses and ketoses classes of organic chemical compounds.

The monosaccharide may comprise dietary monosaccharides comprising at least one of galactose, glucose and fructose.

The disaccharides comprise at least one of lactose and maltose.

The oligosaccharide may comprise at least one of starch and starch-derivatives.

The at least one of starch and starch-derivatives may comprise at least one of glucose syrup, maltodextrin and dextrin.

Other aspects of the invention are also disclosed.

DESCRIPTION OF EMBODIMENTS

For the purposes of promoting an understanding of the principles in accordance with the disclosure, reference will now be made to the embodiments described herein. It will nevertheless be understood that no limitation of the scope of the disclosure is thereby intended. Any alterations and further modifications of the inventive features illustrated herein, and any additional applications of the principles of the disclosure as illustrated herein, which would normally occur to one, skilled in the relevant art and having possession of this disclosure, are to be considered within the scope of the disclosure.

Before the Dental Caries Status Disclosing Solution and associated methods therefor are disclosed and described, it is to be understood that this disclosure is not limited to the particular configurations, process steps, and materials disclosed herein as such may vary somewhat. It is also to be understood that the terminology employed herein is used for the purpose of describing particular embodiments only, and is not intended to be limiting since the scope of the disclosure will be limited only by the claims and equivalents thereof.

In describing and claiming the subject matter of the disclosure, the following terminology will be used in accordance with the definitions set out below.

It must be noted that, as used in this specification and the appended claims, the singular forms "a," "an," and "the" include plural referents unless the context clearly dictates otherwise.

As used herein, the terms "comprising," "including," "containing," "characterised by," and grammatical equivalents thereof are inclusive or open-ended terms that do not exclude additional, unrecited elements or method steps.

It should be noted in the following description that like or the same reference numerals in different embodiments denote the same or similar features.

In the embodiments that follow, there is disclosed a dental Caries Status Disclosing Solution (CSDS) for carious lesions, processes for the preparation and methods of utilisation thereof.

The CSDS comprises an improved water-based silver fluoride solution and a reducing agent solution.

The CSDS comprising a water-based silver fluoride solution for use in the initial application of the water-based silver fluoride solution to a carious lesion followed by the subsequent application of a reducing agent solution for the visual analysis of the status of the carious lesion wherein the water-based silver fluoride solution comprises nitric acid to stabilise the silver fluoride solution.

Specifically, the water-based silver fluoride solution is firstly applied to a carious lesion. Thereafter, after a period of approximately 1 to 3 minutes, the reducing agent solution is applied to the carious lesion to turn the lesion black.

Over a period of time, the lightning of the colour of the blackened carious lesion from black to, for example, between brown and yellow, is an indication that the caries is still progressing. However, the carious lesion remaining black is an indication that the caries is arrested and is no longer progressing.

Now, as alluded to above, the water-based silver fluoride solution is stabilised with nitric acid. The water-based silver fluoride solution stabilised in this was surprisingly found to have an improved shelf life when compared to water-based silver fluoride without the nitric acid stabiliser. Furthermore, the water-based silver fluoride solution does not require ammonia as do prior art arrangements.

In further embodiments, the reducing agent solution has improved clarity when compared to prior art solutions.

Silver Fluoride Solution

The preferred embodiment, the silver fluoride solution comprises silver fluoride having a concentration of between 2% and 75% (w/v).

Now, for the purposes of stabilising the silver fluoride solution, nitric acid is added to the silver fluoride solution.

Specifically, as alluded to above in the background section, a water-based silver fluoride solution shows a reduction in the silver ion levels of approximately 30% after 30 days at 55° C. (being equivalent to 9 months at ambient temperature of 23° C.) thereby requiring the prior art stabilisation methodology of utilising ammonia, albeit with the aforedescribed disadvantages.

As such, in lieu of the prior art utilisation of ammonia, nitric acid is utilised instead as a water-based silver fluoride stabilisation agent. Specifically, in an experiment, we observed no significant deterioration of the silver ions in solution after 60 days at 55° C. (being equivalent to 18 months at ambient temperature of 25° C.) when the water-based silver fluoride solution is stabilised with nitric acid. As such, in embodiments, the improved water-based silver fluoride solution may have a shelf life of more than approximately 18 months without requiring refrigeration.

Preferably, the nitric acid comprises between 3-5% (w/v) of the water-based silver fluoride solution. As such, the nitric acid may bring the pH of the silver fluoride solution down to approximately pH 5.5-6.0.

As nitric acid used in the manufacture of CSDS is 99.4% weight per unit volume, in order to obtain a 3% solution of nitric acid 3.02 ml of the nitric acid is added to 100 ml of water-based silver fluoride.

Alternatively, to obtain a 5% solution of nitric acid in 100 ml of silver fluoride, 5.03 ml of 99.4% nitric acid (w/w) is added to the aqueous silver fluoride.

The silver fluoride solution may be made by dissolving powdered silver fluoride in water.

The water may be ultra-purified and may be de-oxygenated, such as by being purged with argon gas. Purging with argon gas removes dissolved oxygen from the water and is important for reducing the possibility of oxidation of the silver ions.

As such, in accordance with one exemplary process, the process for making the water-based silver fluoride solution comprises adding silver fluoride powder to approx. 85 ml of argon purged water to bring the volume of the water and the silver fluoride powder to approx. 93 ml. Then, nitric acid of between 3.02-5.03 mls is added and the final volume (to 100 mls) is made up by adding a small additional amount of argon purged water. This formula may be scaled to any quantity required.

Reducing Agent Solution

In a preferred embodiment, the reducing agent solution comprises a reducing agent having a concentration of between 1% and 50% (w/v) of the reducing agent solution.

Differing types of reducing agent solutions may be utilised as is described in further detail below.

In a preferred embodiment, the reducing agent solution comprises a stannous fluoride solution. In this regard, the stannous fluoride concentration comprises between approximately 1% and 50% stannous fluoride (w/v).

Now, prior art stannous fluoride solutions are typically cloudy when first prepared. Furthermore, we suspect that mechanised mixing of the stannous fluoride solution contributes to the hydrolysis thereof.

As such, the preparations of the stannous fluoride solution in accordance with present embodiments preferably comprises hand mixing and further preferably the addition of glycerol which surprisingly results in a substantially clear solution.

It should be noted that other inorganic metallic salts may be utilised such as ferrous fluoride in substantially the same concentration of approximately between 1% and 50% (w/v).

Furthermore, organic reducing agents may be utilised substantially in the same ratios of approximately between 1% and 50% (w/v). In these embodiments, the organic reducing agent may comprise tannic acid, polyphenol, eugenol or any type of phenylpropanoid.

Moreover, the reducing agent solution may comprise a sugar acting as a reducing agent on account of the free aldehyde or ketone group. Such sugars include monosaccharides, disaccharides, oligosaccharides, and polysaccharides. The monosaccharides may comprise those of the aldoses and ketoses classes of organic chemical compounds including common dietary monosaccharides including galactose, glucose and fructose. The disaccharides may comprise lactose and maltose.

Furthermore, the reducing agent solution may comprise oligosaccharides such as starch and starch-derivatives including glucose syrup, maltodextrin and dextrin that contain percentages of reducing sugars present in these starch derivatives called dextrose equivalent (DE).

Furthermore, polysaccharides that can be broken down into smaller units, such as glucose or maltose may be used.

As can be appreciated from the foregoing, the CSDS disclosed herein may be made by dissolving silver fluoride powder in water, preferable ultra-pure water and de-oxygenated by purging with argon such that this silver fluoride solution of present embodiments is water-based.

Nitric acid may then be added to the water-based silver fluoride solution to stabilise the water-based silver fluoride solution.

It should be note that, according to the present embodiments, the silver fluoride powder is dissolved in water or the silver fluoride solution is water-based, distinguishing the present water-based solution from silver diamine fluoride which is silver fluoride powder dissolved in ammonia (a solution of water and ammonia).

Now, whereas prior water based silver fluoride solutions (i.e. those not stabilised by nitric acid as per present embodiments) lost more than 5% of the silver. Prior to 2002 no TGA (Therapeutic Goods Administration) auditing of the shelf life was required for specification compliance. In other words, it didn't matter from a compliance perspective if the specified levels of silver were not at optimal levels.

Conversely, the present process of adding nitric acid stabilises the silver ion levels (being one of the active components) such that the present water-based silver fluoride can be given a shelf life of 18 months and more (up to 24 months) which would pass any random TGA audits during this period.

Interpretation

Embodiments:

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the above description of example embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description of Specific Embodiments are hereby expressly incorporated into this Detailed Description of Specific Embodiments, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Different Instances of Objects

As used herein, unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

Specific Details

In the description provided herein, numerous specific details are set forth. However, it is understood that embodiments of the invention may be practiced without these specific details. In other instances, well-known methods, structures and techniques have not been shown in detail in order not to obscure an understanding of this description.

Comprising and Including

In the claims which follow and in the preceding description of the invention, except where the context requires otherwise due to express language or necessary implication, the word "comprise" or variations such as "comprises" or "comprising" are used in an inclusive sense, i.e. to specify the presence of the stated features but not to preclude the presence or addition of further features in various embodiments of the invention.

Any one of the terms: including or which includes or that includes as used herein is also an open term that also means including at least the elements/features that follow the term, but not excluding others. Thus, including is synonymous with and means comprising.

Scope of Invention

Thus, while there has been described what are believed to be the preferred embodiments of the invention, those skilled in the art will recognize that other and further modifications may be made thereto without departing from the spirit of the invention, and it is intended to claim all such changes and modifications as falling within the scope of the invention. For example, the formulas given above are merely representative of procedures that may be used.

Although the invention has been described with reference to specific examples, it will be appreciated by those skilled in the art that the invention may be embodied in many other forms.

INDUSTRIAL APPLICABILITY

It is apparent from the above, that the arrangements described are applicable to manufacturers of consumable dental materials.

The invention claimed:

1. A dental [Caries Status Disclosing Solution] *solution* comprising a water-based silver fluoride solution [for use in the initial application of the silver fluoride solution to a carious lesion followed by the subsequent application of a reducing agent solution for the visual analysis of the status of the carious lesion] wherein the water-based silver fluoride solution comprises nitric acid to stabilise the water-based silver fluoride solution,

*wherein the nitric acid is added to bring the pH of the silver fluoride solution down to approximately pH 5.5-6.0.*

2. The solution as claimed in claim 1, wherein the water-based silver fluoride solution comprises silver fluoride of between 2% to 75% (w/v).

3. The solution as claimed in claim 2, wherein the nitric acid is added in sufficient quantity to substantially stabilises the silver fluoride solution such that the silver ion levels do not decrease by more than 5% over a period of at least 9 months at approximately 25° C.

4. The solution as claimed in claim 2, wherein the nitric acid is added in sufficient quantity to substantially stabilises the silver fluoride solution such that the silver ion levels do not decrease by more than 5% over a period of at least 18 months at approximately 25° C.

5. The solution as claimed in claim 2, wherein the nitric acid is approximately 3 -5% (w/v) of the [Caries Status Disclosing Solution] *dental solution*.

[6. The solution as claimed in claim 2, wherein the nitric acid is added to bring the pH of the silver fluoride solution down to approximately pH 5.5-6.0.]

7. The solution as claimed in claim 1, wherein the water-based silver fluoride solution is made by dissolving powdered silver fluoride in water.

8. The solution as claimed in claim 7, wherein the water is ultrapure water.

9. The solution as claimed in claim 1, wherein the water is de-oxygenated.

10. The solution as claimed in claim 9, wherein the water is purged with argon gas.

11. The solution as claimed in claim 1, wherein the *dental solution includes a second dental solution including a* reducing agent solution comprising an inorganic metallic salt.

12. The solution as claimed in claim 11, wherein the metallic salt has a concentration between 1% to 50% (w/v) of the reducing agent solution.

13. The solution as claimed in claim 12, wherein the metallic salt is ferrous fluoride.

14. The solution as claimed in claim 13, wherein the metallic salt is stannous fluoride.

15. The solution as claimed in claim 14, wherein glycerol is added during the preparation of the stannous fluoride.

16. The solution as claimed in claim 1, wherein the *dental solution includes a second dental solution including a* reducing agent solution comprising an organic reducing agent.

17. The solution as claimed in claim 16, wherein the organic reducing agent has a concentration of between 1% to 50% (w/v) of the reducing agent solution.

18. The solution as claimed in claim 17, wherein the organic reducing agent comprises at least one of tannic acid, a polyphenol, eugenol and a phenylpropanoid.

19. The solution as claimed in claim 1 wherein the *dental solution includes a second dental solution including a* reducing agent solution comprising a sugar comprising at least one of an oligosaccharide, a polysaccharide, a monosaccharide and a disaccharide.

20. The solution as claimed in claim 19, wherein the monosaccharide comprises at least one of aldoses and ketoses classes of organic chemical compounds, wherein the monosaccharide comprises dietary monosaccharides comprising at least one of galactose, glucose and fructose, wherein the disaccharides comprise at least one of lactose and maltose, wherein the oligosaccharide comprises at least one of starch and starch-derivatives and , wherein the at least one of starch and starch-derivatives comprise at least one of glucose syrup, maltodextrin and dextrin.

* * * * *